(12) United States Patent
Ostergaard

(10) Patent No.: US 6,648,006 B1
(45) Date of Patent: Nov. 18, 2003

(54) VALVE AND A METHOD OF CLOSING A VALVE

(75) Inventor: Jan Ostergaard, Frederikshavn (DK)

(73) Assignee: Ostergaard Maskinfabrik A/S, Saeby (DK)

( * ) Notice: Subject to any disclaimer, the term of this patent is extended or adjusted under 35 U.S.C. 154(b) by 0 days.

(21) Appl. No.: 09/937,914

(22) PCT Filed: Mar. 30, 2000

(86) PCT No.: PCT/DK00/00157

§ 371 (c)(1),
(2), (4) Date: Oct. 1, 2001

(87) PCT Pub. No.: WO00/60258

PCT Pub. Date: Oct. 12, 2000

(30) Foreign Application Priority Data

Mar. 31, 1999 (DK) .......................................... 1999 00442

(51) Int. Cl.[7] ............................ B08B 3/00; B08B 9/027; F16K 51/00
(52) U.S. Cl. .................... 137/241; 73/863.86; 134/99.1; 134/166 C; 134/171; 137/614.13; 137/614.18; 137/614.19; 137/15.04; 251/252; 251/331; 251/335.2
(58) Field of Search ................................ 137/238, 240, 137/241, 312, 614.18, 614.19, 15.04, 15.05, 614.13, 15.06, 251/144, 331, 335.2, 252; 73/863.81, 863.86; 134/99.1, 102.1, 166 C, 171

(56) References Cited

U.S. PATENT DOCUMENTS

| | | | | | |
|---|---|---|---|---|---|
| 1,155,576 | A | * | 10/1915 | Isley ........................... | 251/252 |
| 2,855,176 | A | * | 10/1958 | Boteler ........................ | 251/252 |
| 4,015,631 | A | * | 4/1977 | Hayes .......................... | 251/252 |
| 4,293,117 | A | * | 10/1981 | Mueller ........................ | 251/252 |
| 4,350,322 | A | * | 9/1982 | Mueller ........................ | 251/252 |
| 4,423,641 | A | | 1/1984 | Ottung ......................... | 137/240 |
| 4,458,543 | A | * | 7/1984 | Mieth ....................... | 73/863.86 |
| 4,653,526 | A | * | 3/1987 | Hoiss .......................... | 137/241 |
| 4,836,236 | A | * | 6/1989 | Ladisch ....................... | 137/241 |
| 4,979,527 | A | * | 12/1990 | Mueller et al. ............. | 137/241 |
| 5,296,197 | A | * | 3/1994 | Newberg et al. .......... | 73/863.86 |
| 5,549,134 | A | * | 8/1996 | Browne et al. ............ | 137/241 |
| 6,056,003 | A | * | 5/2000 | Madsen et al. ............. | 137/241 |

FOREIGN PATENT DOCUMENTS

WO        WO 9012972 A1        11/1990

* cited by examiner

*Primary Examiner*—George L. Walton
(74) *Attorney, Agent, or Firm*—Kilpatrick Stockton LLP

(57) ABSTRACT

Valve (1) with a through-going axial bore (4), a first spindle (5) axially displaceable in the bore (4), an elastic/flexible seal (10) placed at the one end surface (6) of the first spindle (5), at least two hollow connection branches (7, 8), each of which connects the valve to an outer coupling, said first spindle (5) in a first position forming a first annular sealing surface (9) between the outer surface of the seal (10) and the inner bottom (11) of the valve body which contains the outlet opening (29), and where the first spindle (5) lies coaxially inside a second axially displaceable and hollow spindle (12) lying in the bore (4), the end surface of which or parts thereof (13) form a second annular sealing surface (14) between the outer surface of the seal (10) and the inner bottom (11) of the valve body at a second position radially from the first annular sealing surface (9). There is hereby achieved a valve whereby it is possible to take samples without any risk of contamination of the place at which the samples are taken, and thus ensure that the samples taken will be correct.

10 Claims, 5 Drawing Sheets

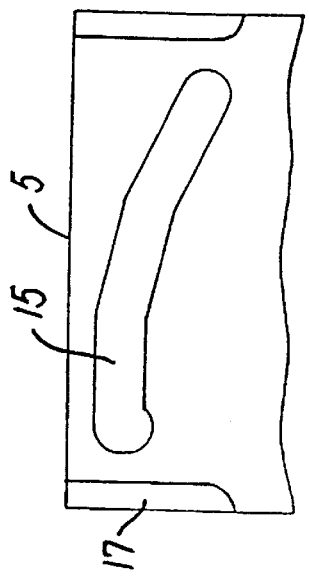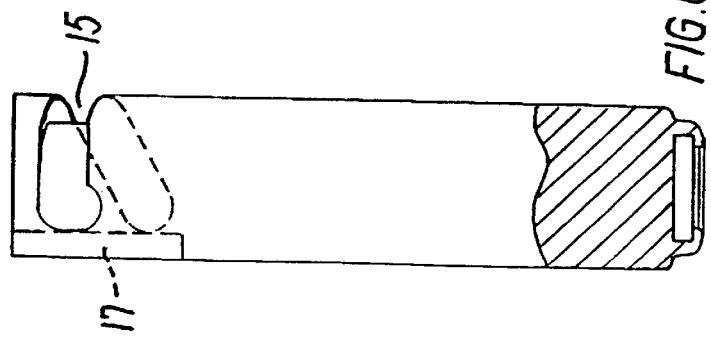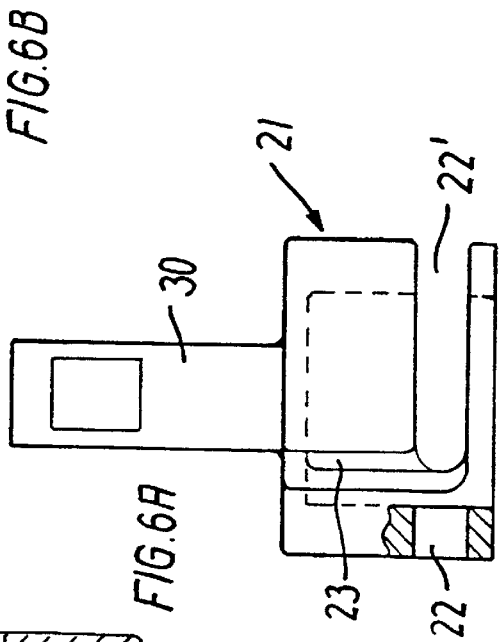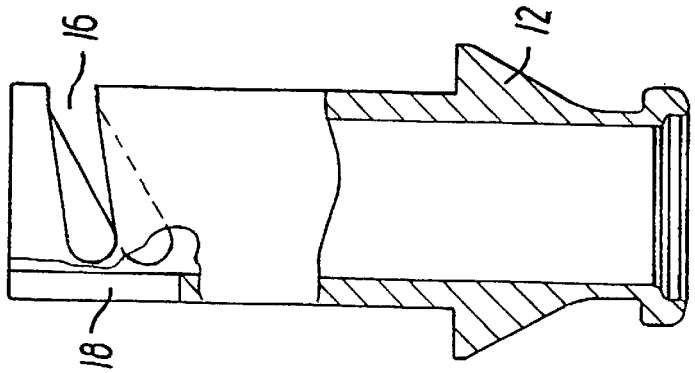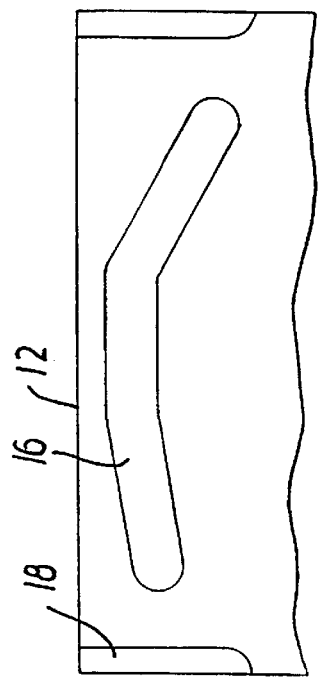

VALVE AND A METHOD OF CLOSING A VALVE

Figure 1:
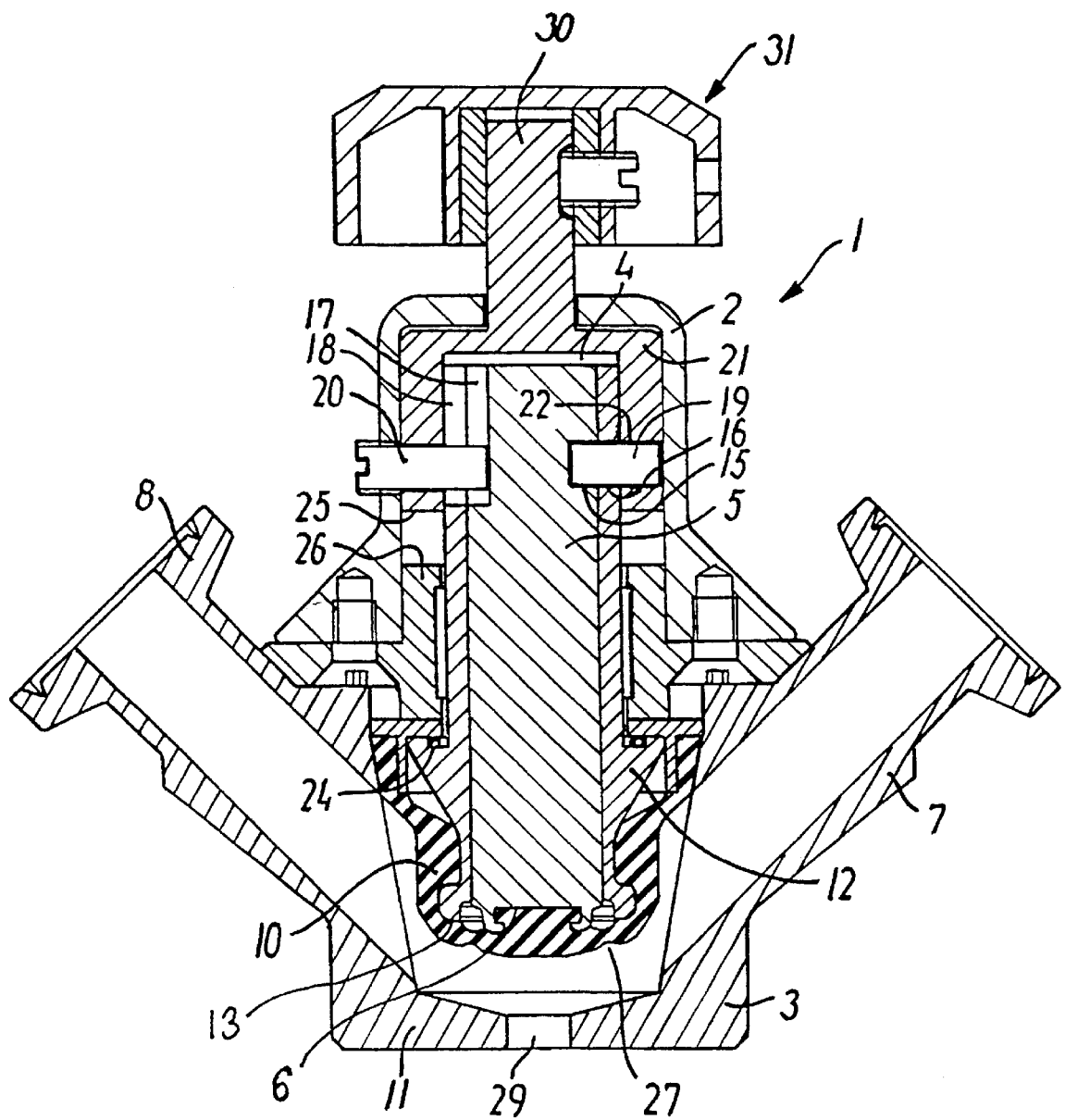

The invention concerns a valve with a through-going axial bore, a first spindle axially displaceable in the bore, an elastic/flexible seal placed at the one end surface of the first spindle, at least two hollow connection branches each of which connects the valve to an outer coupling, said first spindle in a first position forming a first annular sealing surface between the outer surface of the seal and the inner bottom of the valve body, which contains the outlet opening. The invention also concerns a method of closing a valve.

From EP 468,957 a valve is known for the taking of samples, e.g. within the foodstuffs industry, where the bottling of milk, fruit juices and the like is carried out, and where there is a need for an aseptically-sealing valve for the taking of the samples. Such an aseptic seal is also suitable within, for example, the pharmaceutical industry. The above-mentioned patent publication discloses such a valve which can be used for this purpose, but where between the spindle lying in the valve housing and the bottom of the valve housing, a seating is formed solely by closing against the container from which the sample is to be removed. There hereby arises a risk that a contamination of the seating occurs, whereby bacteria can be transferred in connection with the actual taking of the sample, whereby the result of the sample-taking is not correct.

It is thus desirable to provide a valve whereby it is possible to carry out the sample-taking without any risk of contamination occurring at the place at which the sample is taken, and thus that the samples taken are not incorrect.

This object is achieved with a valve of the kind disclosed in the preamble, and also where the first spindle lies coaxially inside a second axially displaceable and hollow spindle lying in the bore, the end surface of which or parts thereof form a second annular sealing surface between the outer surface of the seal and the inner bottom of the valve body at a second position radially from the first annular sealing surface.

The manner in which the valve functions is thus that a double sealing is achieved between the spindles and the bottom, so that the outermost annular seating can be disinfected by steam being blown in through one of the connection stubs when this outermost seating is not activated and when the first seating is activated, i.e. when the inner spindle is at the bottom. This position will typically be held for a period of a minute, during which the disinfection takes place. Hereafter, the outer seating will be activated by the outer spindle moving to the bottom, whereby an annular sealing surface is formed around the annular sealing surface of the first seating.

Hereafter, the inner spindle can be drawn back, whereby the inner seating is inactivated, after which a sample can be taken by the drawing back of the outer seating, in that the bacterial flora which is now on the inner seating originates exclusively from the container in which the valve is mounted, which means that the sampling which takes place will reflect the correct condition, and in that the outer seating, as explained above, has been sterilised by means of the steam.

The spindles can be activated mechanically, but can also be activated by means of compressed air, where the controlling of this takes the movement pattern between the two spindles into account.

By providing a valve according to the invention and as further disclosed in claim 2 and 3, an expedient manner is achieved in which to bring about the movement pattern between the first and second spindle.

By providing a valve according to the invention and as further disclosed in claim 4, it is avoided that the spindles execute a rotating movement, but exclusively execute the axial movement, which is of great importance when the spindles are at the bottom during the formation of both first and second seating.

By providing a valve according to the invention and as further disclosed in claim 5 and 6, the possibility is achieved of activating the spindles mechanically.

By providing a valve according to the invention and as further disclosed in claim 7 and 8, it is achieved that the two seatings are well-defined and with a well-defined separation.

The invention also concerns a method as disclosed in claim 9 and 10, by which method it is achieved that there does not occur a transfer of bacteria between the samples which are taken.

Figure 2:
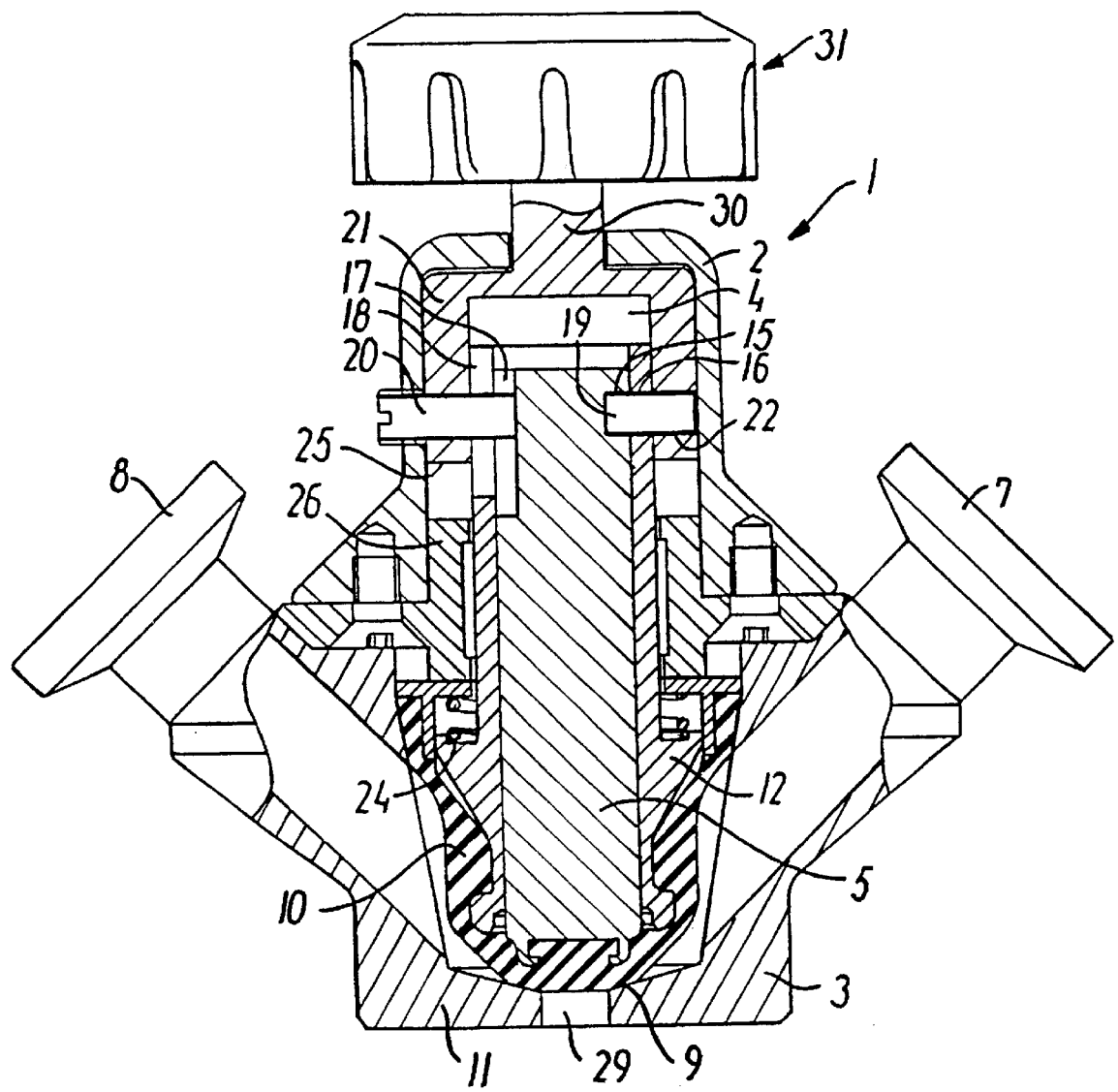
Figure 3:
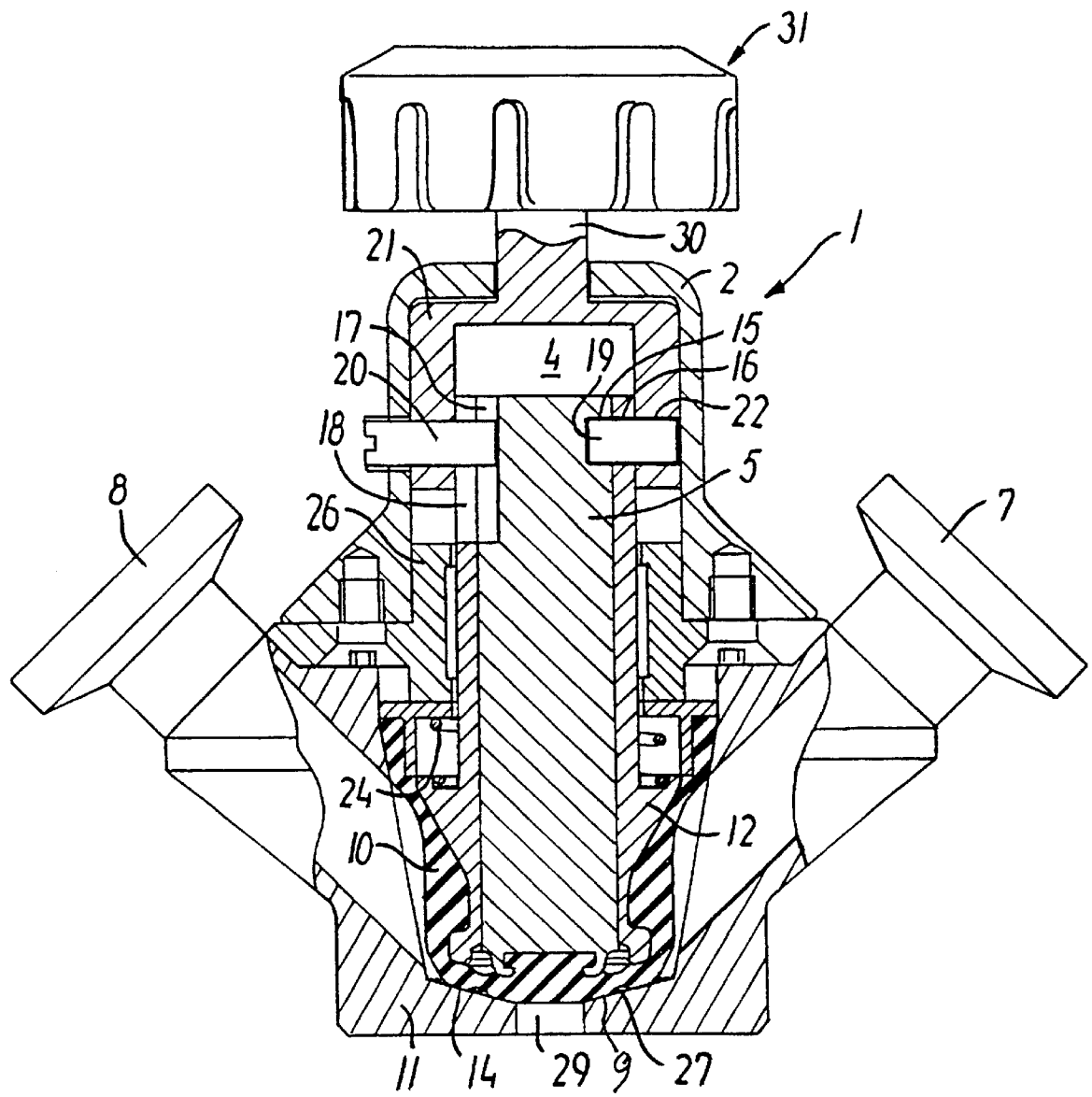
Figure 4:
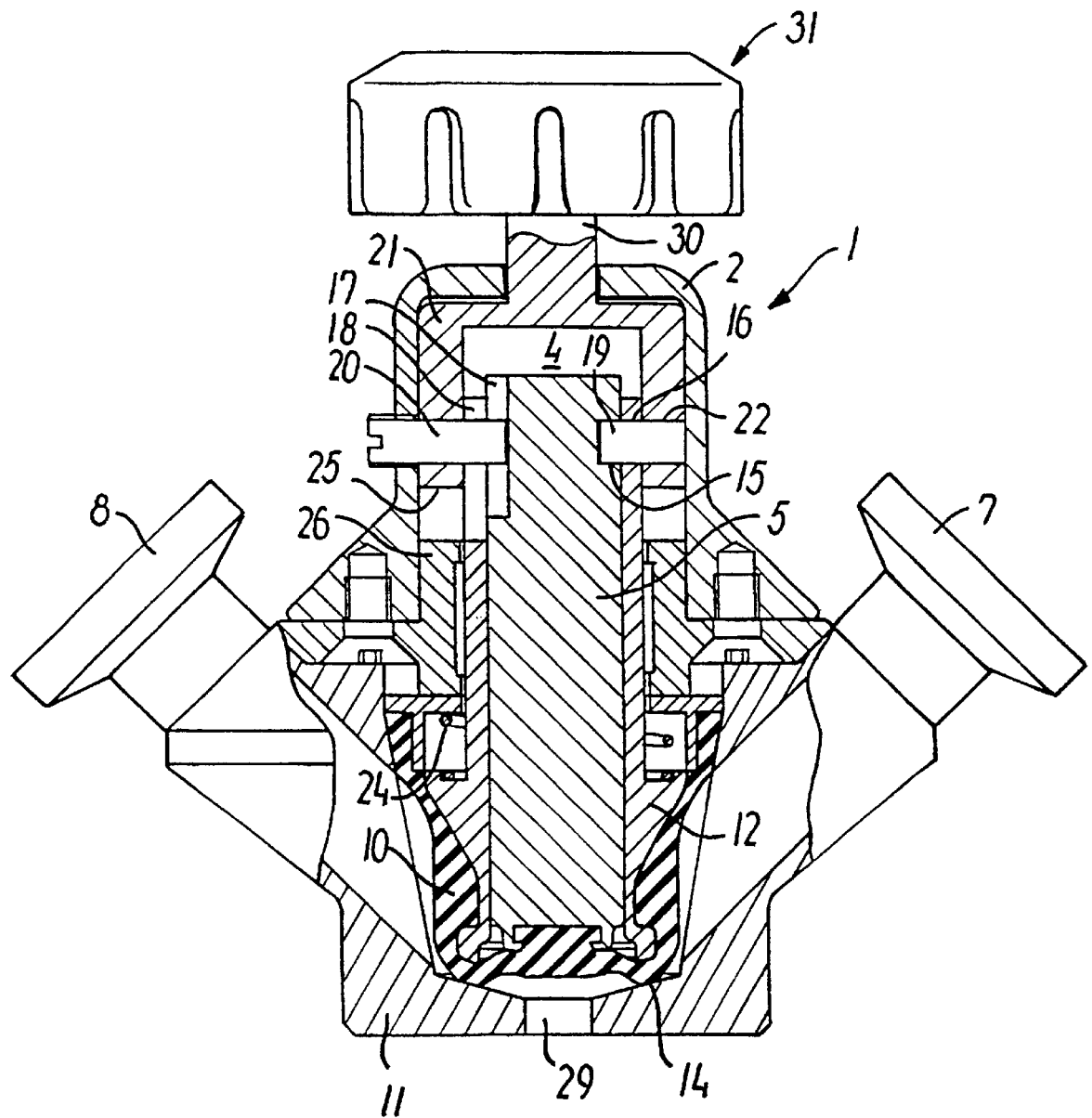

The invention will now be explained in more detail with reference to the drawing, where FIG. 1 shows a valve according to the invention shown in section, where both seatings are inactive, FIG. 2 shows the valve shown in FIG. 1, where only the innermost seating is active, FIG. 3 shows the valve shown in FIG. 1, where both the outer seating and the inner seating are active, FIG. 4 shows the valve shown in FIG. 1, where only the outer seating is active, FIG. 5a is a sectional view of the outer spindle, FIG. 5b shows the periphery of the outer spindle, where the slots are disposed and in unfolded perspective, FIG. 6a shows a sectional view of the inner spindle, FIG. 6b shows the periphery of the inner spindle, where the slots are disposed and in unfolded perspective, and FIG. 7 shows a sectional view of the auxiliary housing.

FIGS. 1–4 show an example embodiment of a valve 1 seen in section, which comprises a valve housing shell 2 connected with bolts to a valve body 3. The valve housing shell 2 and valve body have a bore 4 in their center axis, and in which bore there is disposed a solid first spindle 5, said first spindle 5 being axially parallel with the bore 4, and where said first spindle 5 lies in a hollow second spindle 12 which is axially parallel with the remainder. The spindles are axially moveable in the bore.

The valve 1 further comprises preferably two connection stubs, a first connection branch 7 and a second connection branch 8 lying diametrically opposite to the first connection branch 7, and which are possibly connected to an element for the taking of samples, for example a bottle where the one is concerned, and where the second is concerned to e.g. steam which is blown in for the disinfection of the valve.

When the spindles are in the bottom position, an annular passage is hereby formed between the two connection branches 7, 8.

Between the spindles and the valve housing shell 2 there is provided an auxiliary housing 21, the inner surface of which is congruent with the outer surface of the second spindle 12. Opposite this auxiliary housing, and at the end surfaces 6, 13 of the first and second spindles, there is mounted a seal 10 of a flexible and elastic material, which seal can form a sealing closure between the spindles on the one side and the outlet opening 29 of the valve 1 on the other side, which outlet opening 29 lies in the bottom 11 of the valve body and is parallel with the axis of the bore.

Under the lower end edge 25 of the auxiliary housing there is mounted a bush 26, under which a coil spring 24 is inserted coaxially with the first and second spindle.

FIG. 1 shows the case in which both spindles are at a maximum distance away from the opening 29, whereby there is free passage between the stubs 7, 8 to the valve opening 29.

FIG. 2 shows activation of the first spindle 5, which is pressed to the bottom, whereby the valve seal 10 lies up against the bottom 11 of the valve body and forms a first seating 9 which is an annular sealing surface surrounding the valve opening 29. Hereafter, the second spindle 12 is activated, this being a hollow cylinder in which the first spindle is disposed, and where by an axial movement said second spindle is pressed with its end surface against the bottom 11 of the valve body, whereby the seal which surrounds this spindle is pressed against the bottom 11 of the valve body and forms a new annular sealing surface, designated the second annular sealing surface 14, which lies in a radial manner to the first. This is shown in FIG. 3. Between these two sealing surfaces thus formed, the seal is expediently provided with a groove 27, whereby a well-defined demarcation of the two seatings takes place. The seal can be configured as a membrane, for example as disclosed in EP 468,957. The seal can also be effected by two O-rings or the like lying coaxially.

The seal/membrane ensures that there is a tight closure towards the rest of the valve in the area over the two connection branches 7, 8.

FIG. 4 shows the situation where the first spindle 5 is drawn back, whereby the first annular sealing surface 9 is inactivated, and whereby there is only the second annular sealing surface 14.

As shown in FIGS. 5–6, the movement pattern between the two spindles arises by said spindles being provided with both vertical and helical slots/recesses. At the upper end and opposite that end at which the seal is placed, in the wall of the outer spindle 12, which is configured as a cylinder with walls of 1–2 mm, there is formed a through-going slot 16 with a breadth of a few mm, and which slot extends in a slightly helical manner, in the sense that the first third part of the slot in the unfolded plane extends at a slight angle upwards, corresponding to approx. 5° to the horizontal plane. Thereafter, for the next third part the slot extends horizontally, and for the last third part it angles down towards the seal forming an angle of approx. 20° to the horizontal. The way in which this slot extends is shown in FIG. 5b, where the spindle is "folded out". This section also shows the slot 18 extending vertically from the upper end edge, and at a distance from this corresponding approx. to the lower end of the helical slot.

The corresponding slot 15 in the inner spindle is seen in FIG. 6b, the wall of this spindle similarly comprising a slot with a length which extends for approx. ¾ of the periphery of the spindle and with a depth in the solid spindle of approx. 1–2 mm. Unlike the slot in the outer spindle, this slot extends in another manner, in that the first third part extends horizontally, the next third part extends at a slight angle to the horizontal and downwards towards the seal corresponding to approx. 5°, and where the last third part angles down more sharply towards the seal and corresponding to approx. 15–20° to the horizontal. Moreover, in this spindle there is also a vertically-extending slot 17 with the same length as that seen indicated in the outer spindle.

The object of the vertical slots is to ensure that the spindles do not describe a rotating movement with their axial movements. With reference to FIG. 2, the axial movement is brought about by the helical slot 15 in the inner spindle being connected by a pin to the corresponding helical slot 16 in the outer spindle, said helical slot 16 in turn being connected to the auxiliary housing 21 where the pin is possibly led through a circular hole 22. The pin does not extend through the valve housing shell, and is a loosely-mounted pin. On the opposite side, a second pin 20 is placed in a vertical slot and engages in the vertical slot 17 in the inner spindle, in the vertical slot in the outer spindle 18 and finally in the horizontal slot 22 in the auxiliary housing 21, which also comprises a vertical slot 23. The pin is fastened to the valve housing shell 2, or extends through this, in that the pin can be formed as a screw.

The auxiliary housing 21 has a cylindrical rod 30 which extends in extension of the axis of the bore and protrudes out of an opening in the valve housing shell 2, and when a turning of the auxiliary housing 21 is effected by the turning of a knob 31, these forces will be transferred via the pins to both the outer and the inner spindle, which due to the mutual positioning, dimensions and angles of the slots will describe the movements indicated in FIGS. 1–4, and where the vertical slots ensure that no rotation takes place between the two spindles, but exclusively axial movements.

The movement pattern between the two spindles can also be brought about by means of compressed air which is activated by a control mechanism which ensures the desired movement pattern. In this case the spindles are not configured with slots, and the auxiliary housing becomes superfluous. In this case it is important that tight seals are provided between the individual components.

The valve 1 will thus be mounted with its valve body 3 on the container from which a sample is desired to be taken, and where the valve will effect a closure out towards the outside. A sample will be taken via one of the connection stubs, and a disinfection of the interior of the valve will be effected via the second connection stub, preferably by means of steam. The starting point for the use of the valve will thus be FIG. 1, which shows the valve inactive with free communication to the inside of the container.

FIG. 2 shows how the inner seating 9 is activated and effects a closing-off of the insides of the container. In this position, the annular sealing surface 14 can be disinfected by the spraying-in of steam. This position will typically be held for approx. one minute. Thereafter, the sealing surface 14 can be activated, whereby a closing-off of the inner sealing surface 9 or first seating takes place as shown in FIG. 3.

Finally, as shown in FIG. 4, the inner spindle is brought to the drawn back position, whereby there is a free inwards communication. Hereafter, the inner and the outer spindles are brought into their most withdrawn positions as shown in FIG. 1, and whereby it is now possible for the sample to be taken, and this sampling is not contaminated in that the outer seating has had the inner seating closed-off, and in that the inner seating has been active during the sterilisation of the outer seating, which means that no transfer of bacteria occurs from the taking of one sample to the taking of the next.

FIG. 7 shows a sectional view of the auxiliary housing 21, in which there is a vertical slot 23 which in length corresponds to the spindle slots, and an annular, through-going slot 22 in the wall and extending for approx. ¾ of the periphery, and which lies at the same level all the way around.

What is claimed is:

1. A valve (1) comprising:
   a through-going axial bore (4);
   a first spindle (5) axially displaceable in the bore (4);
   an elastic/flexible seal (10) placed at one end surface (6) of the first spindle (5);
   at least two hollow connection branches (7,8) for withdrawal of samples, each of which connects the valve to an outer coupling;
   said first spindle (5) in a first position forming a first annular seating surface (9) between the outer surface of the seal (10) and an inner bottom (11) of the valve body which contains an inlet opening (29) from which samples are drawn into the valve;

the first spindle (5) lies coaxially inside a second axially displaceable and hollow spindle (12) lying in the bore (4); and the end surface of the second spindle or parts thereof (13) forming a second annular seating surface (14) between the outer surface of the seal (10) and the inner bottom (11) of the valve body at a second position radially spaced from the first annular seating surface (9).

2. Valve according to claim 1, characterised in that the surface of the first spindle (5) is configured with an outer annular slot (15) for approx. ¾ of its periphery.

3. Valve according to claim 1, characterized in that approx. ¾ of the wall of the second spindle (12) is configured with an annular slot (16), said slot (16) extending through the wall, and in that a loose pin (19) is placed in the slot (16) and engages in the slot (15) in the first spindle.

4. Valve according to claim 1, characterized in that the first (5) and the second (12) spindle are each configured with a vertical slot (17, 18), said vertical slot (18) in the second spindle extending through the wall, and in which slot a pin (20) is placed, said pin (20) being in firm connection with the valve housing shell (2) of the valve (1) and engaging in the slot (17) in the first spindle via the slot (18) in the second spindle.

5. Valve according to claim 1, characterized in that an auxiliary housing (21) is mounted between the valve housing shell (2) of the valve and the second spindle (2).

6. Valve according to claim 1, characterized in that a helical spring (24) is inserted coaxially with the first (5) and second spindle (12).

7. Valve according to claim 1, characterized in that the seal (10) between the first (9) and second seating (14) is configured with an annular recess/groove (27).

8. Valve according to claim 6, characterized in that the seal comprises two coaxial O-rings.

9. The valve of claim 1, further comprising:

the first and second spindles being selectably operative to:

an open state in which both spindles are moved to respective open positions in which the outer surface of the seal (10) is withdrawn from the first (9) and second (14) annular seating surfaces, whereby a sample is taken from the inlet opening (29) and communicates to one of the connection branches (7,8), a cleaning state in which the first spindle (5) is moved to a closed position to engage the seal (10) with the first annular seating surface (9) while the second spindle (12) remains at the open position with the seal withdrawn from the second annular seating surface (14), whereby the second annular seating surface (14) remains exposed to disinfection by introducing a disinfecting fluid through one of the connection branches (7,8);

a transition state in which the second spindle (12) is moved to a closed position to engage the seal (10) with the second annular seating surface (14) while the first annular seating surface (9) remains closed, whereby the disinfected second annular seating surface (14) remains uncontaminated; and to a closed state in which the first spindle (5) is moved to the open position in which the seal (10) is withdrawn from the first annular seating surface (9) and the second spindle (12) remains at the closed position, whereby the inlet opening (29) is open to sample material while the second annular seating surface (14) remains closed to the connection branches (7,8).

10. Method for the closing of a valve with a through-going axial bore, a first spindle axially displaceable in the bore, an elastic/flexible seal placed at the one end surface of the first spindle, at least two hollow connection branches for withdrawal of samples, each of which connects the valve to an outer coupling, said first spindle moving in an axial movement towards the bottom of the inner body of the valve in bringing about a first position, in which position a first seating forms an annular sealing surface between the outer surface of the seal and the inner bottom of the valve body which contains an inlet opening; and a second spindle, in which spindle the first spindle is disposed, the second spindle being movable downwards into its bottom position by an exclusively axial movement for the formation of a second seating in a second position; comprising the steps of:

operating the valve to an open state in which both spindles are moved to respective open positions in which the outer surface of the seal is withdrawn from the first and second annular seating surfaces, whereby a sample is taken from the inlet opening and communicated to one of the connection branches, operating the valve to a cleaning state in which the first spindle is moved to a closed position to engage the seal with the first annular seating surface while the second spindle remains at the open position with the seal withdrawn from the second annular seating surface, whereby the second annular seating surface remains exposed to disinfection by introducing a disinfecting fluid through one of the connection branches;

operating the valve to a transition state in which the second spindle is moved to a closed position to engage the seal with the second annular seating surface while the first annular seating surface remains closed, whereby the disinfected second annular seating surface remains uncontaminated; and operating the valve to a closed state in which the first spindle is moved to the open position in which the seal is withdrawn from the first annular seating surface and the second spindle remains at the closed position, whereby the inlet opening is open to sample material while the second annular seating surface remains closed to the connection branches.

* * * * *